US00PP28640P3

(12) United States Plant Patent
Kobayashi

(10) Patent No.: US PP28,640 P3
(45) Date of Patent: Nov. 14, 2017

(54) POINSETTIA PLANT NAMED 'PER7_13'

(50) Latin Name: ***Euphorbia pulcherrima* Willd.**
Varietal Denomination: 'PER7_13'

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 113 days.

(21) Appl. No.: 14/998,483

(22) Filed: Jan. 9, 2016

(65) Prior Publication Data

US 2017/0202125 P1 Jul. 13, 2017

(51) Int. Cl.
*A01H 5/02* (2006.01)

(52) U.S. Cl.
USPC ..... Plt./305

(58) Field of Classification Search
USPC ..... Plt./263.1, 302, 303, 305
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER7_13', characterized by its relatively compact, uniform, upright and mounded plant habit; moderately vigorous growth habit; freely and upright to somewhat outwardly branching habit; very dark green-colored leaves; large inflorescences with golden yellow-colored flower bracts; and good post-production longevity.

2 Drawing Sheets

Botanical designation: *Euphorbia pulcherrima* Willd.
Cultivar denomination: 'PER7_13'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER7_13'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant is a naturally-occurring whole plant mutation of *Euphorbia pulcherrima* Willd. 'PER1409', disclosed in U.S. Plant Pat. No. 27,850. The new Poinsettia plant was discovered and selected by the Inventor as a single flowering plant from within a population of plants of 'PER1409' in a controlled greenhouse environment in Encinitas, Calif. on Sep. 6, 2012.

Asexual reproduction of the new Poinsettia plant by terminal vegetative cuttings in a controlled greenhouse environment in Encinitas, Calif. since January, 2013 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER7_13'. These characteristics in combination distinguish 'PER7_13' as a new and distinct Poinsettia plant:

1. Relatively compact, uniform, upright and mounded plant habit.
2. Moderately vigorous growth habit.
3. Freely and upright to somewhat outwardly branching habit.
4. Very dark green-colored leaves.
5. Under natural season conditions, plants flower on or about November 17 in Southern California.
6. Large inflorescences with golden yellow-colored flower bracts.
7. Good post-production longevity.

In side-by-side comparisons conducted in Encinitas, Calif., plants of the new Poinsettia differ primarily from plants of the mutation parent, 'PER1409', in the following characteristics:

1. Plants of the new Poinsettia are more compact than plants of 'PER1409'.
2. Plants of the new Poinsettia and 'PER1409' differ in fully expanded flower bract color as plants of 'PER1409' have light yellow and peach-colored flower bracts with dark pink-colored flecks and spots.

Plants of the new Poinsettia can be compared to plants of the *Euphorbia pulcherrima* Willd. 'PER10606', disclosed in U.S. Plant Pat. No. 20,351. In side-by-side comparisons conducted in Encinitas, Calif., plants of the new Poinsettia differed primarily from plants of 'PER10606' in the following characteristics:

1. Plants of the new Poinsettia were more compact than plants of 'PER10606'.
2. Plants of the new Poinsettia were more upright than plants of 'PER10606'.

3. Plants of the new Poinsettia and 'PER10606' differed in flower bract color as plants of 'PER10606' had creamy white-colored flower bracts.
4. Plants of the new Poinsettia flowered about ten days later than plants of 'PER10606' when grown under natural season conditions in Southern California.

Plants of the new Poinsettia can be compared to plants of the *Euphorbia pulcherrima* Willd. 'PER975', disclosed in U.S. Plant Pat. No. 16,882. In side-by-side comparisons conducted in Encinitas, Calif., plants of the new Poinsettia differed primarily from plants of 'PER975' in the following characteristics:

1. Plants of the new Poinsettia were more compact than and not as vigorous as plants of 'PER975'.
2. Plants of the new Poinsettia had darker green-colored leaves than plants of 'PER975'.
3. Plants of the new Poinsettia and 'PER975' differed in flower bract color as plants of 'PER975' had light pink to pale yellow-colored flower bracts.
4. Plants of the new Poinsettia flowered about four days earlier than plants of 'PER975' when grown under natural season conditions in Southern California.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side to top perspective view of a typical flowering plant of 'PER7_13' grown in a container.

The photograph on the second sheet is a close-up view of a typical flowering plant of 'PER7_13'.

DETAILED BOTANICAL DESCRIPTION

Plants used in the aforementioned photographs and in the following detailed description were grown during the late autumn/early winter in quart (plants for the photographs) and 16.5-cm containers (plants used for the description) in a polyethylene-covered greenhouse in Encinitas, Calif. under natural season conditions and cultural practices typical of commercial Poinsettia production. During the production of the plants, day temperatures averaged 26° C., night temperatures averaged 18° C. and light levels averaged 5,000 foot-candles. Measurements and numerical values represent averages for typical flowering plants. Plants were pinched one time and were 19 and 25 weeks old for the quart and 16.5-cm containers, respectively, when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER7_13'.

Parentage: Naturally-occurring whole plant mutation of *Euphorbia pulcherrima* Willd. 'PER1409', disclosed in U.S. Plant patent application Ser. No. 14/545,486.

Propagation:

*Type.*—Terminal vegetative cuttings.

*Time to initiate roots.*—About seven to ten days at night temperatures about 20° C. and day temperatures about 27° C.

*Time to produce a rooted young plant.*—About four weeks at night temperatures about 20° C. and day temperatures about 27° C.

*Root description.*—Fibrous; typically white in color, actual color of the roots is dependent on substrate composition, water quality, fertilizer type and formulation, substrate temperature and physiological age of roots.

Plant description:

*Plant and growth habit.*—Relatively compact, uniform, upright and mounded plant habit; inverted triangle; large inflorescences with numerous flower bracts positioned above the foliar plane; moderately vigorous growth habit.

*Plant height.*—About 33 cm.

*Plant diameter or spread.*—About 45 cm.

*Lateral branch description.*—Quantity: Freely branching habit, about six to seven lateral branches develop after pinching; upright branching habit. Length: About 28 cm. Diameter: Thick, about 7.5 mm. Internode length: About 1.5 cm to 2 cm. Strength: Strong. Aspect: About 30° to 45° from vertical. Texture: Smooth, glabrous. Luster: Moderately glossy. Color: More green than 146A.

*Leaf description.*—Arrangement: Alternate, simple. Length: About 10.25 cm. Width: About 7.75 cm. Shape: Ovate. Apex: Acuminate. Base: Mostly obtuse with truncate or cuneate tendencies. Margin: Mostly entire. Aspect: Outwardly to slightly upright; keeled. Texture, upper and lower surfaces: Smooth, glabrous; prominent venation on lower surface. Luster, upper surface: Slightly glossy. Luster, lower surface: Matte. Venation pattern: Pinnate, arcuate. Color: Developing and fully expanded leaves, upper surface: Much darker green than 147A; venation, close to 146A to 146B. Developing and fully expanded leaves, lower surface: Close to 147A; venation, close to 146B. Leaf petioles: Length: About 3.8 cm to 4.7 cm. Diameter: Thick, about 4 mm to 5 mm. Texture, upper and lower surfaces: Smooth, glabrous. Luster, upper and lower surfaces: Moderately glossy. Color, upper and lower surfaces: Close to 146B.

Inflorescence description:

*Inflorescence type and habit.*—Terminal inflorescences are compound corymbs of cyathia with numerous colored flower bracts subtending the cyathia; inflorescences uniformly positioned above the foliar plane.

*Fragrance.*—None detected.

*Flowering response.*—Under natural season conditions, plants typically flower on or about November 17 in Southern California; under artificial long nyctoperiod/short photoperiod conditions, plants flower about seven to eight weeks later.

*Post-production longevity.*—Good post-production longevity; plants of the new Poinsettia maintain good substance and flower bract color for about four to six weeks under interior conditions; flower bracts persistent and cyathia not persistent.

*Inflorescence diameter.*—About 29 cm.

*Inflorescence height (depth).*—About 5 cm.

*Flower bracts.*—Quantity per inflorescence: Numerous, about 33. Length, largest bracts: About 11.25 cm. Width, largest bracts: About 9.75 cm. Shape: Ovate. Apex: Acuminate. Base: Mostly obtuse with truncate tendencies. Margin: Entire. Aspect: Mostly horizontal to slightly upright; keeled. Texture, upper and lower surfaces: Smooth, glabrous; satiny. Luster, upper and lower surfaces: Matte. Venation pattern: Pinnate, arcuate. Color: Developing or transitional bracts, upper surface: Ground color, darker green than 147A; irregular and random sectors, slightly more yellow than 163D. Developing or transitional bracts, lower surface: Ground color, close to 146A; irregular and random sectors, close to 153C and 16B. Fully expanded bracts, upper surface: Close to between N163D and 23A; occasionally tinged with close to 25A; color does not fade with development. Fully expanded bracts, lower surface: Close to between 20A and 21B; color does not fade with development. Bract petioles: Length: About 4.1 cm. Diameter: Thick about 4 mm. Texture, upper and lower surfaces: Smooth, glabrous. Luster, upper and lower surfaces: Moderately glossy. Color, upper and lower surfaces: Close to N144A.

*Cyathia.*—Quantity per corymb: About 12 to 15. Length: About 9 mm. Width: About 4.5 mm. Shape: Ovoid. Texture: Smooth, glabrous. Color, inner and outer surfaces: Close to 144A to 144B.

*Nectaries.*—Quantity per cyathium: One. Length: About 6 mm. Width: About 5 mm. Shape: Roughly elliptical. Texture: Smooth, glabrous. Color, inner and outer surfaces: Close to 17A.

*Peduncles.*—Length: About 5 mm. Diameter: About 2 mm. Strength: Strong. Aspect: Mostly upright to slightly outwardly. Texture: Smooth, glabrous. Color: Close to 144A to 144B.

*Reproductive organs.*—Stamens: Quantity per cyathium: About 12 to 15. Filament length: About 5 mm. Filament color: Close to 145C. Anther shape: Round to oval; bi-lobed. Anther length: Less than 1 mm. Anther color: Close to 15A. Amount of pollen: Scarce to none. Pollen color: Close to 15A. Pistils: Quantity per cyathium: One; tri-parted. Pistil length: About 8 mm. Stigma shape: Lanceolate, six-parted, recurved. Stigma color: Close to 186A. Style length: About 6.5 mm. Style color: Close to 144B to 144C. Ovary color: Close to 144B.

*Seeds and fruits.*—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER7_13' as illustrated and described.

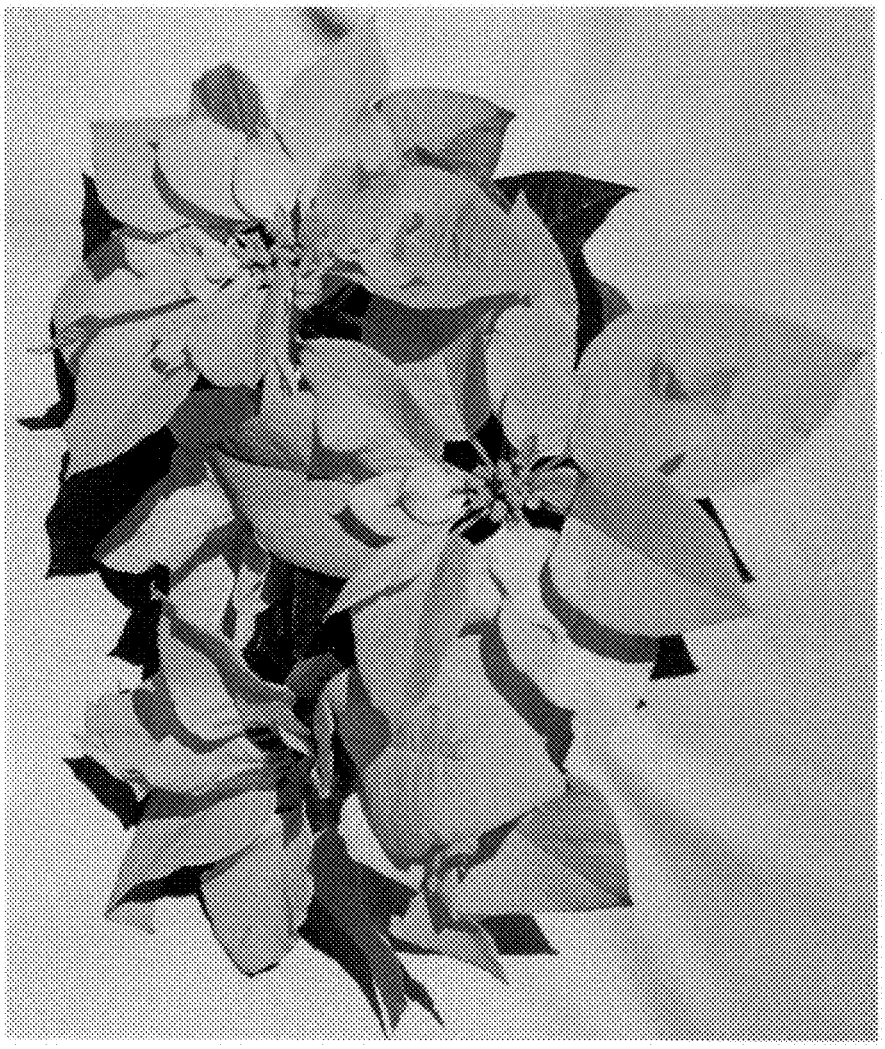

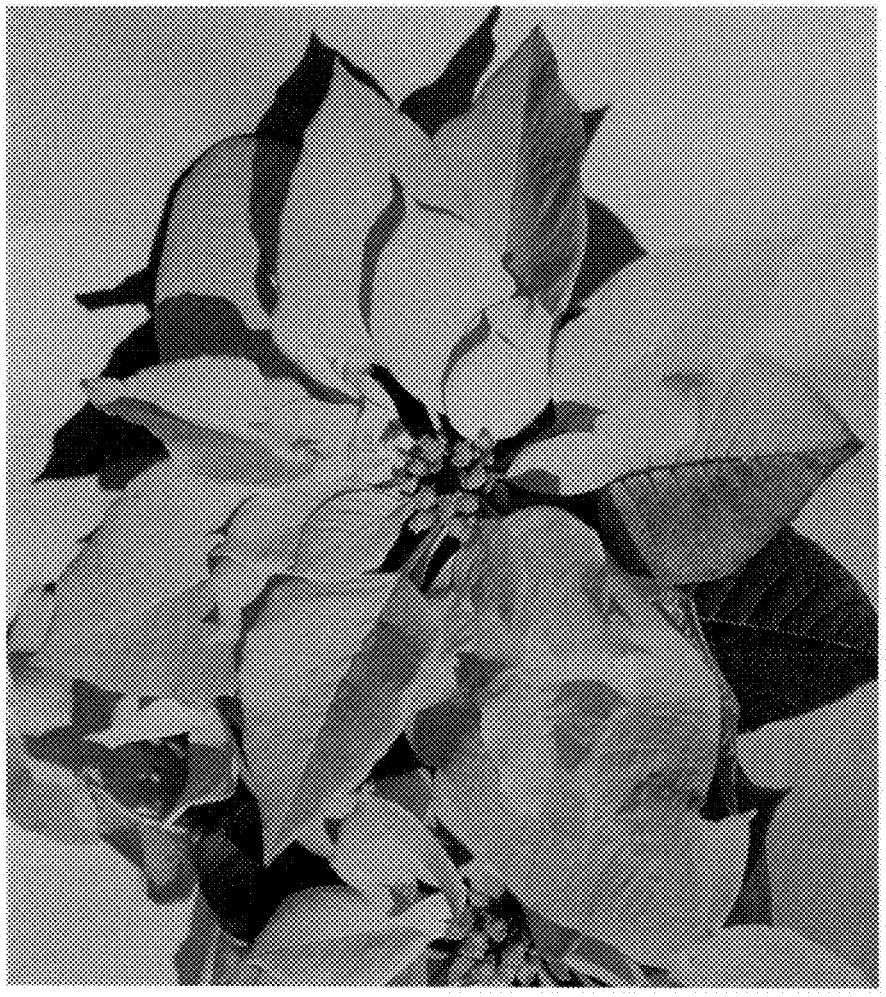

* * * * *